United States Patent [19]

Struve et al.

[11] Patent Number: 4,973,431

[45] Date of Patent: Nov. 27, 1990

[54] PROCESS FOR THE RECOVERY OF METHYL-BRANCHED, SATURATED $C_{14}$–$C_{24}$-FATTY ACIDS

[75] Inventors: Alfred Struve, Hilden; Horst Baumann, Leichlingen; Karl H. Schmid, Mettmann; Alfred Meffert, Monheim, all of Fed. Rep. of Germany

[73] Assignee: Henkel Kommanditgesellschaft auf Aktien, Duesseldorf-Holthausen, Fed. Rep. of Germany

[21] Appl. No.: 319,507

[22] Filed: Mar. 6, 1989

[30] Foreign Application Priority Data

Mar. 7, 1988 [DE] Fed. Rep. of Germany ....... 3807409

[51] Int. Cl.$^5$ ............................ C11B 7/00; C11C 3/12
[52] U.S. Cl. .................................... 260/409; 260/412; 260/420
[58] Field of Search ....................... 260/409, 412, 420

[56] References Cited

U.S. PATENT DOCUMENTS 2,293,676  8/1942  Myers et al. ......................... 260/419
2,812,342  11/1987 Peters et al. ......................... 260/409

OTHER PUBLICATIONS

J. Am. Oil Chem. Soc., (vol. 62) pp. 888–891, (1985).

Primary Examiner—Werren B. Lone
Assistant Examiner—Vera C. Clarke
Attorney, Agent, or Firm—Ernest G. Szoke; Wayne C. Jaeschke; Daniel S. Ortiz

[57] ABSTRACT

A process for the isolation and purification of essentially fatty acid mixtures, which in addition to the methyl branched fatty acids contain saturated and unsaturated, respectively straight chain as well as methyl branched, unsaturated fatty acids, in which the industrial fatty acid mixtures are first hydrogenated by catalysis and then the methyl branched saturated fatty acids are separated, and in which before the hydrogenation if necessary, a separation by the hydrophilization process is provided, this process produces the desired products with a high yield and purity.

12 Claims, No Drawings

PROCESS FOR THE RECOVERY OF METHYL-BRANCHED, SATURATED $C_{14}$-$C_{24}$-FATTY ACIDS

BACKGROUND OF THE INVENTION

1. Field of the Invention:

The invention is a process for the isolation or purification of essentially methyl branched saturated $C_{14}$–$C_{24}$ fatty acids from hydrogenated industrial fatty acid mixtures. The industrial fatty acid mixtures contain methyl branched saturated $C_{14}$–$C_{24}$ fatty acids saturated or unsaturated straight chain $C_{10}$–$C_{24}$ fatty acids as well as methyl branched unsaturated $C_{14}$–$C_{24}$ fatty acids. The industrial fatty acid mixtures are catalytically hydrogenated and the essentially methyl branched saturated $C_{14}$–$C_{24}$ fatty acids, contained in the hydrogenated fatty acid mixture, are separated from the saturated straight chain $C_{10}$–$C_{24}$ fatty acids. The methyl branched $C_{14}$–$C_{24}$ fatty acids can be further purified by known processes such as by distillation.

2. Statement of Related Art:

Methyl branched, saturated and unsaturated $C_{10}$–$C_{24}$ fatty acids occur as a by-product in the thermal or catalytic dimerization of the corresponding unsaturated straight chain fatty acids. The structure of the "so-called" isostearic acids formed in the dimerization of tall oil fatty acids has been described, cf. J. Am. Oil Chem. Soc. (1979), Vol. 56, pp. 823A–827A; ibid. (1974), Vol. 51, pp. 522–527; ibid. (1985), Vol. 62, 888–891.

Isostearic acids are liquid at ambient temperature and resistant to oxidation due to their saturated nature. They are therefore useful products, particularly in the formulation of lubricants and as components of cosmetic preparations and textile treatment agents. Several processes for the isolation and purification of isostearic acids from fatty acid mixtures obtained during the dimerization of fatty acids have been described. U.S. Pat. No. 2,812,342, for example, discloses a process according to which the industrial fatty acid mixtures, produced during the dimerization of $C_{18}$ a fatty acids, are hydrogenated with known nickel catalysts and hydrogen under pressure and the isostearic acids obtained are isolated according to a process disclosed in U.S. Pat. No. 2,293,676, namely by dissolving in a suitable solvent and crystallizing out at reduced temperatures.

BRIEF SUMMARY OF THE INVENTION

Other than in the operating examples, or where otherwise indicated, all numbers expressing quantities of ingredients or reaction conditions used herein are to be understood as modified in all instances by the term "about".

It is now found that methyl branched saturated $C_{14}$–$C_{24}$ fatty acids can be obtained without use of a solvent from hydrogenated industrial fatty acid mixtures, by means of a hydrophilization process. The hydrophilization process is a known process principle, cf. Ullmann's Encyclopedia of Industrial Chemistry, 5th. edition, Vol. A10, pp. 265–266 (1987), which is incorporated herein by reference, for the separation of stearic acid from industrial oleic acid mixtures; it can also be described as fractional crystallization in the presence of wetting agents.

The process of the invention is accordingly characterized in that the methyl branched saturated $C_{14}$–$C_{24}$ fatty acids are separated from the straight chain, saturated $C_{10}$–$C_{24}$ fatty acids of hydrogenated industrial fatty acid mixtures by a hydrophilization process. The hydrophilization can be multistage.

DETAILED DESCRIPTION OF THE INVENTION

The process of the invention can be used to recover the methyl branched saturated fatty acids from industrial fatty acid mixtures which contain methyl branched saturated and may also contain methyl branched unsaturated $C_{14}$–$C_{24}$ fatty acids. It is preferred that the industrial fatty acid mixtures contain mainly $C_{16}$–$C_{22}$ fatty acids which occur during the dimerization of the corresponding unsaturated fatty acids particularly of fatty acid mixtures high in unsaturated $C_{18}$ a fatty acids.

Separation by the hydrophilization process according to the invention, encounters difficulties with hydrogenated industrial fatty acid mixtures which contain more than 30% by weight of stearic acid. When the stearic acid level is above 30% by weight, a dispersion of the saturated straight chain fatty acids does not form or forms only with difficulty.

According to a further preferred embodiment of the invention, industrial fatty acid mixtures which would be expected to have a stearic acid content of more than 30 % by weight after the hydrogenation, are subjected, before the catalytic hydrogenation, to a pre-separation by the hydrophilization process to separate a portion of the saturated straight chain $C_{10}$–$C_{24}$ fatty acids from the mixture.

The hydrogenation of the unsaturated fatty acids contained in the industrial fatty acid mixtures can be effected with the known palladium or nickel catalysts at high pressure and temperatures; preferred hydrogenation temperatures lie between 150 and 220° C. Apart from this the hydrogenation conditions correspond to those of a usual fatty acid solidification, cf. Ullmann's Encyclopedia of Industrial Chemistry, (1977) Vol. A10, pp. 267–269 which is incorporated herein by reference.

According to a further preferred embodiment of the invention, to separate the methyl branched saturated $C_{14}$–$C_{24}$ fatty acids from the hydrogenated mixture, the fatty acid mixtures, catalytically hydrogenated are subjected to a two-stage hydrophilization process in which the separation temperature of the second separation stage is at least 10° C. below that of the first separation stage. In this process the methyl branched saturated fatty acid fraction, obtained in the first stage, is subjected to a second separation, by the hydrophilization process at a lower temperature to remove additional fractions of saturated straight chain fatty acids. The second separation stage generally immediately follows the first separation stage.

The invention is explained in more detail by the following preferred embodiments.

The monomeric fatty acid used in the examples was obtained as a by-product in the dimerization of tall oil fatty acid.

The monomeric fatty acid used had the following analytical values:

Acid number (AN) 173.7

Saponification number (SN) 184.1

Iodine number (IN) according to Kaufmann 69.5

Hydrogenated iodine number (HIN) with Pd/C in glacial acetic acid at 20° C. and approx. 1 bar hydrogen) 40

Unsaponifiable parts 8.0

Rising melting point 31° C.

The gas chromatographic analysis with pentadecanoic acid as the internal standard, indicated 5.5 by weight % palmitic acid, 12.2% by weight stearic acid as well as 12% by weight "oleic acids" (9-octadecanoic acid, elaidic acid and position-isomeric octadecanoic acids). The main quantity of the fatty acids consisted of methyl branched fatty acids which exited the column in the peak range between palmitic and stearic acid, and which were not accurately quantifiable.

The Examples are presented to show one skilled in the art how to carry out the invention. The Examples are not intended to limit the invention to the preparation, temperatures, time and concentrations disclosed.

EXAMPLE 1

200 g of the monomeric fatty acid was hydrogenated with 2 g of Pd/C-catalyst (5 % Pd on charcoal; Engelhard catalyst) and 20 bar hydrogen at 200° C. The hydrogenated fatty acid product separated from the catalyst, had an iodine number of 15.2.

An amount of 150 g of the solidified monomeric fatty acid was added in a molten state, at approx. 50° C., to a so-called "Schaber stirrer" (a cylindrical vessel made of high grade steel, provided with a cooling jacket, with a flat bottom and a U-shaped stirrer fitted tightly to the wall) together with 112.5 g of a wetting agent solution at about 50° C. (weight ratio of monomeric fatty acid to wetting agent solution 1 : 0.75). The wetting agent solution consisted of water (98.7% by weight), 0.33 g (0.3% by weight) sodium decyl sulfate and 1.12 g (1% by weight) of magnesium sulfate. Water at a temperature of 20° C. was passed through the cooling jacket of the Schaber stirrer. The mixture of fatty acid and wetting agent solution was brought to a crystallization temperature with stirring at approx. 60 revolutions per minute. After 40 minutes a further 187.5 g of wetting agent solution at 20° C. was added. The mixture was stirred for another 5 minutes at 20 ° C. The resulting thin fluid dispersion was centrifuged in a beaker centrifuge (Heraeus Christ Company) at 4000 revolutions per minute for 5 minutes. The dispersion separated into a lighter liquid methyl branched fatty acid phase which was predominantly wetting agent free and a heavier phase, consisting of the aqueous wetting agent solution and the crystalline fractions of straight chain, saturated fatty acids dispersed therein. After separation of the methyl branched fatty acid fraction, the water phase with the fatty acid crystals (mp less than 60° C.) was separated into a fatty acid phase and a water phase in a separating tube heated to 90°. The separated fractions of liquid and solid fatty acids are as regards weight 69.5 : 31.3. The solid fraction has an iodine number of 2 and a melting point of 46 to 48° C., the liquid part has an iodine number of 19.3 and a turbidity point of 16 ° C.

EXAMPLE 2

40 kg of melted monomeric fatty acid was cooled from about 50° C. to 20 to 22° C. in a vessel with a grid stirrer fitted close to the wall, together with 30 kg of the wetting agent solution described in Example 1 (weight ratio 1 : 0.75) with stirring at approx. 60 revolutions per minute, by passing water at 19° to 20° C. through the cooling jacket of the vessel.

With continued stirring, a further 50 kg of the wetting agent solution warmed to 20° C. was added (weight ratio of fatty acid : wetting agent solution in total 1 : 2). After a further approx. 20-minute period of stirring the thin fluid dispersion formed was separated using a bowl centrifuge. The dispersion separated into a lighter, liquid, fatty acid phase containing little wetting agent solution (approx. 5% by weight), and into a heavier phase of wetting agent solution with fatty acid crystals dispersed therein. The fatty acid division by weight, was 85 (liquid) : 15 solid).

After the completion of the separation process in the centrifuge, both fractions were heated to about 80° C. The separated wetting agent solutions were drained off; and the fatty acids were washed twice with water at 80° C. The liquid fraction was dried in a vacuum (approx. 20 mbar) at 100° C. with stirring and hydrogenated with 2% by weight of a nickel catalyst (containing approx. 25% nickel on kieselguhr) at 200° C. with 20 bar hydrogen. The product separated from the catalyst had an iodine number of 28 and a rising melting point of 36° C.

25 kg of the hardened hydrogenated product was again separated by the hydrophilization process, dispersed and separated in the manner described above, i.e. at 20° C. with the same ratio of fatty acid to wetting agent solution. There resulted a separation of liquid to solid fatty acid in the weight ratio of 74 : 26.

The liquid fatty acid obtained in the previous stage was immediately subjected, when moist with wetting agent solution, to a further separation by the hydrophilization process, in which the cooling began at approx. 40° C. and ended at 10° C. All the remaining stages were carried out as described above.

Separation in the centrifuge then gave a ratio of 89 (liquid) : 11 (solid) by weight.

After the completion of the separation, the liquid fraction was washed and dried as described above in connection with the first separation stage.

The liquid fraction from the last separation stage (89%) was distilled in a vacuum at 0.5 mbar. One obtained:

9 % by weight first fraction (b.p. 50 to 150° C./0.5 mbar)

82 % by weight main fraction (b.p. 150 to 165° C./0.5 mbar)

9.5% by weight residue.

For the methyl branched, saturated fatty acids there was a final yield of 56% by weight (before distillation) or 46% by weight (main fraction of the distillation).

In the following table, the analyses of products of the various separation stages are shown.

TABLE

| Analysis | Separation (parts by weight; liquid:solid) | | | | | | | |
|---|---|---|---|---|---|---|---|---|
| | First Separation | | Second Separation[1] | | Third Separation | | Distillation | |
| | 85 : | 15 | 74 : | 26 | 89 : | 11 | 82[2] : | 9[3] |
| AN | 170 | 192 | 160 | 174 | 161 | 166 | 172 | 99 |
| SN | 181 | 196 | 176 | 186 | 175 | 184 | 183 | 113 |
| IN | 78 | 24 | 33 | 16 | 34 | 22 | 25 | 92 |

TABLE-continued

| | Separation (parts by weight; liquid:solid) | | | | | | | |
|---|---|---|---|---|---|---|---|---|
| | First Separation | | Second Separation[1] | | Third Separation | | Distillation | |
| Analysis | 85 | : 15 | 74 | : 26 | 89 | : 11 | 82[2] | : 9[3] |
| HIN | 42 | 17 | <2 | <2 | <2 | <2 | <2 | — |
| Turbidity point (°C.) | 17 | — | 12 | — | 6 | — | 8 | — |
| mp (°C.) | — | 43–9 | — | 40–3 | — | 30–40 | — | — |
| $C_{16}$ total[4] % by weight | 4.4 | 11 | 3.9 | 7 | 3.5 | 10 | 4.1 | 2.6 |
| $C_{18}$ total[5] % by weight | 3.8 | 51 | 4.1 | 40 | 3.2 | 16 | 4.8 | 0.8 |

[1] with hardened product (IN 28)
[2] main fraction
[3] first fraction
[4] palmitic acid
[5] stearic acid

EXAMPLE 3

The application of the process of the invention, as in Example 1 did not form a dispersion with the following monomeric fatty acid mixture due to the high content of straight chain compounds >30 %). Coarse agglomerates formed.

AN 171.2
SN 182.0
IN 77.8
HIN 38.0
1.8 % palmitic acid by weight
12.5 % stearic acid by weight
19.3 % "oleic acids" by weight A pre-separation was therefore necessary. The monomeric fatty acid mixture was subjected to a separation by the hydrophilization process according to the conditions described under Example 2/1 st separation stage. A division of 13.4% by weight solid fraction with iodine number 34.5 and 86.6% by weight liquid fraction with iodine number 85.9 was achieved. The solid fraction consisted of more than 50% stearic acid. In the liquid fraction the total amount of straight chain fatty acids which would be present in the hydrogenated mixture was clearly under 30% by weight. The prerequisite for the application of the method described in Example 1 was therefore fulfilled. The mixture can be hydrogenated and the methyl branched $C_{14}$–$C_{24}$ fatty acids separated from the hydrogenated mixture as shown in Example 1.

We claim:

1. A process for the isolation of a mixture comprising methyl branched saturated $C_{14}$–$C_{24}$ fatty acids from a fatty acid mixture which contains saturated and unsaturated methyl branched $C_{14}$–$C_{24}$ fatty acids and saturated and unsaturated $C_{10}$–$C_{24}$ fatty acids which comprises:
   (a) catalytically hydrogenating the fatty acid mixture to form a hydrogenated fatty acid mixture; and
   (b) separating the mixture comprising methyl branched saturated $C_{14}$–$C_{24}$ fatty acids from the hydrogenated fatty acid mixture by hydrophilization.

2. A process of claim 1 wherein the fatty acid mixture contains mainly $C_{16}$–$C_{22}$ fatty acids.

3. A process of claim 1 wherein the fatty acid mixture, before hydrogenation, is treated by hydrophilization to reduce the amount of stearic acid in the mixture when the amount of stearic acid in the mixture, after hydrogenation, is above about 30% by weight.

4. A process of claim 2 wherein the fatty acid mixture, before hydrogenation, is treated by hydrophilization to reduce the amount of stearic acid in the mixture when the amount of stearic acid in the mixture, after hydrogenation, is above about 30% by weight.

5. A process of claim 1 wherein the hydrogenated fatty acid mixture is separated into a liquid fatty acid phase and an aqueous phase containing solid fatty acid, by the hydrophilization process at a first separation temperature, the liquid fatty acid phase is separated from the aqueous phase and subjected to a second hydrophilization process in which the separation temperature is at least about 10° C. lower than the first separation temperature.

6. A process of claim 2 wherein the hydrogenated fatty acid mixture is separated into a liquid fatty acid phase and an aqueous phase containing solid fatty acid, by the hydrophilization process at a first separation temperature, the liquid fatty acid phase is separated from the aqueous phase and subjected to a second hydrophilization process in which the separation temperature is at least about 10° C. lower than the first separation temperature.

7. A process of claim 3 wherein the hydrogenated fatty acid mixture is separated into a liquid fatty acid phase and an aqueous phase containing solid fatty acid, by the hydrophilization process at a first separation temperature, the liquid fatty acid phase is separated from the aqueous phase and subjected to a second hydrophilization process in which the separation temperature is at least about 10° C. lower than the first separation temperature.

8. A process of claim 4 wherein the hydrogenated fatty acid mixture is separated into a liquid fatty acid phase and an aqueous phase containing solid fatty acid, by the hydrophilization process at a first separation temperature, the liquid fatty acid phase is separated from the aqueous phase and subjected to a second hydrophilization process in which the separation temperature is at least about 10° C. lower than the first separation temperature.

9. A process of claim 1 wherein the fatty acid mixture is hydrogenated at a temperature of from about 150° C. to about 220° C. in the presence of a catalyst containing at least one metal selected from the group consisting of palladium and nickel.

10. A process of claim 2 wherein the fatty acid mixture is hydrogenated at a temperature of from about 150° C. to about 220° C. in the presence of a catalyst containing at least one metal selected from the group consisting of palladium and nickel.

11. A process of claim 3 wherein the fatty acid mixture is hydrogenated at a temperature of from about 150° C. to about 220° C. in the presence of a catalyst containing at least one metal selected from the group consisting of palladium and nickel.

12. A process of claim 4 wherein the fatty acid mixture is hydrogenated at a temperature of from about 150° C. to about 220° C. in the presence of a catalyst containing at least one metal selected from the group consisting of palladium and nickel.

* * * * *